(12) United States Patent
Urushihara (10) Patent No.: US 8,764,720 B2
(45) Date of Patent: Jul. 1, 2014

(54) ABSORBENT ARTICLE AND ABSORBENT ARTICLE PACKAGING

(75) Inventor: Makiko Urushihara, Mima-gun (JP)

(73) Assignee: Livedo Corporation, Ehime (JP)

( * ) Notice: Subject to any disclaimer, the term of this patent is extended or adjusted under 35 U.S.C. 154(b) by 0 days.

(21) Appl. No.: 13/509,336

(22) PCT Filed: Nov. 2, 2010

(86) PCT No.: PCT/JP2010/006469
§ 371 (c)(1),
(2), (4) Date: May 11, 2012

(87) PCT Pub. No.: WO2011/080860
PCT Pub. Date: Jul. 7, 2011

(65) Prior Publication Data
US 2012/0228180 A1    Sep. 13, 2012

(30) Foreign Application Priority Data
Dec. 28, 2009   (JP) .................................. 2009-298706

(51) Int. Cl.
*A61F 13/15*    (2006.01)

(52) U.S. Cl.
USPC ........ 604/385.201; 604/385.01; 604/385.101; 604/385.02; 604/379; 604/378

(58) Field of Classification Search
USPC ......... 604/385.01, 385.201, 385.101, 385.02, 604/379, 378
IPC ............. A61F 13/15,13/42; A61L 15/56, 15/24
See application file for complete search history.

(56) References Cited

U.S. PATENT DOCUMENTS

| | | | |
|---|---|---|---|
| 3,430,630 A | | 3/1969 | Megison et al. |
| 4,966,286 A | | 10/1990 | Muckenfuhs |
| 6,702,798 B2 * | | 3/2004 | Christoffel et al. .... 604/385.201 |
| 2006/0184146 A1 | | 8/2006 | Suzuki |
| 2007/0233031 A1 * | | 10/2007 | Benson et al. ........... 604/385.02 |

FOREIGN PATENT DOCUMENTS

| CN | 1758889 A | 4/2006 |
|---|---|---|
| DE | 19915716 C1 | 8/2000 |
| EP | 0406928 A1 | 1/1991 |
| EP | 0778015 A1 | 6/1997 |
| EP | 1290995 A2 | 3/2003 |
| EP | 1609448 A1 | 12/2005 |
| JP | 3048599 B2 | 6/2000 |

(Continued)

OTHER PUBLICATIONS

Office Action from Japanese Patent App. No. 2009-298706 (Jun. 18, 2013) with English language translation thereof.

(Continued)

*Primary Examiner* — Jacqueline F. Stephens
(74) *Attorney, Agent, or Firm* — Cermak Nakajima LLP; Tomoko Nakajima (57) ABSTRACT

An absorbent article comprising an absorbent body including a top sheet, a back sheet and an absorbent laminate disposed between the top sheet and the back sheet, wherein: the absorbent body has a longitudinal direction and a width direction; the absorbent laminate comprises a fiber assembly layer containing pulp fibers, and a sheet-shaped absorbent layer containing an absorbent polymer but not containing a pulp fiber between nonwoven fabric sheets; the absorbent article is folded at a fold line extending in the width direction; and the fiber assembly layer has an opening on the fold line.

10 Claims, 8 Drawing Sheets

(56) References Cited

FOREIGN PATENT DOCUMENTS

| | | |
|---|---|---|
| JP | 2005006954 A | 1/2005 |
| JP | 2006-061396 A | 3/2006 |
| JP | 2006115996 A | 5/2006 |
| JP | 2008136642 A | 6/2008 |
| JP | 2009-153735 A | 7/2009 |
| WO | WO93/09744 A1 | 5/1993 |
| WO | WO96/20668 A1 | 7/1996 |
| WO | WO98/31319 A1 | 7/1998 |
| WO | WO98/43684 A1 | 10/1998 |
| WO | WO00/37002 A1 | 6/2000 |
| WO | WO2004/084785 A1 | 10/2004 |
| WO | WO2009/005431 A1 | 1/2009 |

OTHER PUBLICATIONS

International Search Report for PCT Patent App. No. PCT/JP2010/006469 (Feb. 2, 2011).
Patent Examination Report No. 1 from Australian Patent App. No. 2010337805 (Feb. 18, 2013).
Office Action from Chinese Patent App. No. 201080056737.5 (Sep. 24, 2013) with English translation thereof.
Office Action from Singapore Patent App. No. 201203709-9 (Oct. 2, 2013).
Second Notification of Office Action from Chinese Patent App. No. 201080056737.5 (Jan. 13, 2014) with English translation thereof.
Communication Pursuant to Article 94(3) EPC from European Patent App. No. 10784354.2 (Apr. 23, 2014).

\* cited by examiner

ABSORBENT ARTICLE AND ABSORBENT ARTICLE PACKAGING

This application is a national phase entry under 35 U.S.C. §371 of PCT Patent Application No. PCT/JP2010/006469, filed on Nov. 2, 2010, which claims priority under 35 U.S.C. §119 to Japanese Patent Application No. 2009-298706, filed Dec. 28, 2009, both of which are incorporated by reference.

TECHNICAL FIELD

The present invention relates to an absorbent article such as an incontinence pad (including a light incontinence pad), a sanitary napkin and a disposable diaper, and an absorbent packaging in which the absorbent articles are packaged in a container.

BACKGROUND ART

Conventionally, there is known an absorbent article such as an incontinence pad, and a sanitary napkin, which is folded and individually wrapped with a wrapping material. For a folded absorbent article, in order that a trace of a fold line is less likely to remain when a folded absorbent article is unfolded for use, or a folded absorbent article is easily unfolded, various modifications have been made. For example, Patent Literature 1 discloses an absorbent article comprising an absorbent body, in which a linear groove extending so as to cross a fold line perpendicularly is formed on an external side of the absorbent body in order that the folded absorbent article is easily unfolded. Patent Literature 2 discloses an absorbent article comprising an absorbent body which has a bend area in which a plurality of bend assisting means are provided so as to extend in the width direction of the absorbent body. The absorbent article is folded at the bend area, whereby the trace of the fold line is less likely to remain in the absorbent article.

CITATION LIST

Patent Literature

PTL 1: Japanese Patent Application Laid-Open Publication No. 2006-61396
PTL 2: Japanese Patent Application Laid-Open Publication No. 2009-153735

SUMMARY OF INVENTION

Technical Problem

The present invention has been achieved in view of the above circumstances, and an object of the present invention is to provide an absorbent article with which a trace of a fold line is less likely to remain even when folded.

Solution To Problem

An absorbent article of the present invention which solves the above problems comprises an absorbent body including a top sheet, a back sheet and an absorbent laminate disposed between the top sheet and the back sheet, wherein: the absorbent body has a longitudinal direction and a width direction; the absorbent laminate comprises a fiber assembly layer containing pulp fibers, and a sheet-shaped absorbent layer containing an absorbent polymer but not containing a pulp fiber between nonwoven fabric sheets; the absorbent article is folded at a fold line extending in the width direction; and the fiber assembly layer has an opening on the fold line. In the absorbent article of the present invention, since the absorbent laminate comprises the sheet-shaped absorbent layer and the fiber assembly layer, even when the absorbent article is folded, the pressure which the sheet-shaped absorbent layer receives at the fold line from circumferences is reduced, whereby the fold line is less likely to remain in the sheet-shaped absorbent layer. Moreover since the fiber assembly layer has the opening on the fold line, the sheet-shaped absorbent layer comes to be folded at a part where the opening overlaps, and as a result, the pressure which the sheet-shaped absorbent layer receives at the fold line from circumferences is further reduced, whereby the fold line is less likely to remain in the sheet-shaped absorbent layer. Therefore, when the folded absorbent article is unfolded for use, a trace of the fold line is less likely to remain in the absorbent article, thereby improving the wearing feel of the absorbent article.

The fiber assembly layer preferably has the one opening extending in the longitudinal direction so as to cross both the fold line and a centerline of the absorbent body in the longitudinal direction. When the opening is provided in this manner, the opening tends to be positioned near an urethral orifice of a wearer in wearing, and thus, the wearer is less likely to feel a pressure around the urethral orifice due to the lowered rigidity of the absorbent article at the opening, thereby improving the wearing feel of the absorbent article. In addition, the trace of the fold line is less likely to remain at least near the urethral orifice in the sheet-shaped absorbent layer, thereby improving the wearing feel of the absorbent article.

Preferably, the absorbent article is folded at the one, two or three fold line(s) extending in the width direction, thereby folded in two, three or four; and the opening is provided on at least one of the fold line(s). When the number of the fold lines is not more than three, the sheet-shaped absorbent layer comes to be not folded at excessively number of the fold line, the folded absorbent article can be carried with ease, and packing efficiency of the folded absorbent article in a container is improved.

The absorbent article may further comprise a cover sheet detachably joined to the back sheet by an adhesive layer, the cover sheet may be folded at the fold line together with the absorbent body, and the absorbent body may be wrapped with the cover sheet. When the absorbent body is wrapped with the cover sheet, the individually wrapped absorbent article can be carried with ease. In the absorbent article of the present invention, even when the absorbent article is individually wrapped, the fold line on which the opening is provided can be easily pinched, thereby improving handleability of the absorbent article.

The present invention also provides an absorbent article packaging comprising a container and the absorbent article of the present invention, wherein: a plurality of the absorbent articles are stacked in the container so that the fold lines, on each of which the opening is provided, of all the absorbent articles face in a same direction; and the container has an openable part formed on a side to which the fold lines provided with the openings of the stacked absorbent articles face. In the absorbent article packaging of the present invention, even when the absorbent articles are contained in the container while being compressed, the pressure from the adjacent absorbent articles is reduced at the fold line on which the opening is provided, and hence a gap is likely to occur between the adjacent absorbent articles. Therefore, when the openable part of the container is opened for taking out the absorbent article, the fold line on which the opening is provided can be easily pinched, and thus, it is easy to take out the absorbent article from the container.

Advantageous Effects of Invention

According to the absorbent article of the present invention, the trace of the fold line is less likely to remain in the absorbent article even when the absorbent article is folded.

DESCRIPTION OF EMBODIMENTS

An absorbent article of the present invention comprises an absorbent body including a top sheet, a back sheet and an absorbent laminate disposed between the top sheet and the back sheet, and is folded at a fold line extending in a width direction. In the present invention, the fold line is a line formed as a result of folding the absorbent article, and it is unnecessary to provide the fold line prior to folding. The absorbent article of the present invention is suitably used for an incontinence pad, a sanitary napkin and the like. Since the absorbent article of the present invention is folded at the fold line extending in the width direction of the absorbent body, the absorbent article is folded compactly, so that the absorbent article can be carried with ease and can be easily put into a container. For example, the absorbent article is sold at stores in the state where the absorbent article is packaged in a container.

The absorbent body has a longitudinal direction and a width direction. The longitudinal direction means a direction extending in a front-back direction at a crotch of a wearer when the wearer wears the absorbent article. With respect to the longitudinal direction, an abdomen side of a wearer is referred to as a front side, and a buttocks side of the wearer is referred to as a rear side. The width direction means a direction orthogonal to the longitudinal direction on the same plane as the absorbent body. A direction on the plane formed by the longitudinal direction and the width direction is defined as a planar direction. In addition, in the present invention, upper side means a wearer's side when the absorbent article is worn, and lower side means the side opposite to a wearer when the absorbent article is worn, that is an outer side. In addition, the direction from the upper side to the lower side is referred to as a thickness direction.

The top sheet is a sheet which is located on a wearer's side, that is an inner side, when the absorbent article is worn. The material of the top sheet is not restricted as long as it is liquid-permeable. The back sheet is a sheet which is located on an opposite side of a wearer, that is an outer side, when the absorbent article is worn. The material of the back sheet is not restricted as long as it is liquid-impermeable.

The top sheet and the back sheet may be composed of a nonwoven fabric, a woven fabric, a knitted fabric, a plastic film, a laminate of a plastic film and a nonwoven fabric, or the like. Examples of the laminate include a laminate in which a sheet of a nonwoven fabric and a sheet of a plastic film are stacked, and a laminate in which a plastic film is interposed between nonwoven fabrics. When a plastic film or a laminate including a plastic film is used for the top sheet, it is preferable that pores for allowing liquid to permeate through are formed in the plastic film. The top sheet is preferably made of a nonwoven fabric. The back sheet is preferably made of a nonwoven fabric or a plastic film.

When a nonwoven fabric is used for the top sheet or the back sheet, a nonwoven fabric manufactured by a spunbonding method, an air-through method, a point bonding method, a melt blowing method, an airlaid method, a combination of these methods, or the like, is preferably used. Also, a nonwoven fabric manufactured by an SMS method which is a combination of the spunbonding method and the melt blowing method may be used.

When a nonwoven fabric is used for the top sheet or the back sheet, a material of the nonwoven fabric can be selected as appropriate from synthetic fibers such as polypropylene, polyethylene, polyester (e.g., PET) and polyamide; natural fibers such as pulp and silk. Also, composite fibers can be used as the synthetic fibers. Among them, polypropylene, polyethylene, PET, or composite fibers obtained by combining these materials, are preferred. When such a nonwoven fabric is used, a sheet having a high strength and excellent texture is easily obtained.

An adhesive layer may be provided on the lower side of the back sheet. By the adhesive layer being provided on the lower side of the back sheet, the absorbent article can be fixed to the inner side of a disposable diaper or an underwear such as an underpants, when the absorbent article is used. The adhesive layer is not particularly limited as long as the adhesive layer is capable of adhering to an underwear, a disposable diaper, or the like.

A cover sheet which is detachable from the adhesive layer may also be provided on the lower side of the adhesive layer. In other words, the absorbent article may comprise the cover sheet detachably joined to the back sheet by the adhesive layer in addition to the absorbent body. When the cover sheet is provided, the cover sheet covers the adhesive layer to protect the adhesive layer in an unused state of the absorbent article, and in using the absorbent article, the adhesive force of the adhesive layer is utilized when the cover sheet is peeling off. For the cover sheet, it is only necessary to use a material which is detachable from the adhesive layer, and examples of the cover sheet include, for example, a plastic film, a nonwoven fabric, and a laminate of a plastic film and a nonwoven fabric. The cover sheet may be larger in size than the absorbent body, may be the same in size as the absorbent body, or may be smaller in size than the absorbent body.

The absorbent laminate is provided between the top sheet and the back sheet, and absorbs a bodily fluid such as urine. The absorbent article of the present invention can suitably be used for an incontinence pad, a sanitary napkin, and the like; and absorbent articles used for such applications are required to be formed slimly while having a high absorptive capacity. Therefore, the absorbent laminate comprises a sheet-shaped absorbent layer containing an absorbent polymer but not containing a pulp fiber between nonwoven fabric sheets. Since the sheet-shaped absorbent layer contains the absorbent polymer and does not contain pulp fibers, bulkiness due to pulp fibers is reduced, and therefore, the sheet-shaped absorbent layer can be formed slimly while having a high absorptive capacity.

The sheet-shaped absorbent layer is formed by providing an absorbent polymer between nonwoven fabric sheets, and a pulp fiber is not provided between the nonwoven fabric sheets. Examples of the absorbent polymer provided in the sheet-shaped absorbent layer include polyacrylic acid-based absorbent polymers, starch-based absorbent polymers, and polyvinyl alcohol-based absorbent polymers. Among them, polyacrylic acid-based absorbent polymers such as sodium polyacrylate are preferably used as the absorbent polymer, since they have a high absorptive capacity.

The nonwoven fabric sheets used in the sheet-shaped absorbent layer are liquid-permeable. For such nonwoven fabric sheets, for example, hydrophilic fibers such as cellulose, rayon, and cotton; and hydrophilized hydrophobic fibers such as polypropylene, polyethylene, polyester, and polyamide with a surfactant may be used.

The sheet-shaped absorbent layer, which can be formed so as to be thin and have a high absorptive capacity, has a certain level of hardness even though being thin, since the sheet-shaped absorbent layer does not contain pulp fibers. Therefore, if the sheet-shaped absorbent layer is folded so that a fold line is formed, the fold line is less likely to disappear. In this case, even when the folded absorbent article is unfolded for use, a trace of the fold line is likely to remain in the sheet-shaped absorbent layer, whereby the wearing feel of the absorbent article may deteriorate.

Therefore, in the absorbent article the present invention, the absorbent laminate comprises a fiber assembly layer containing pulp fibers in addition to the sheet-shaped absorbent layer, and an opening is provided at a part of the fiber assembly layer where the fold line for folding the absorbent article is formed. That is, the absorbent laminate comprises the sheet-shaped absorbent layer and the fiber assembly layer; and the fiber assembly layer has an opening on the fold line. The fiber assembly layer contains pulp fibers, thereby formed relatively soft. Therefore, since the absorbent laminate comprises the sheet-shaped absorbent layer and the fiber assembly layer, even when the absorbent article is folded, the pressure which the sheet-shaped absorbent layer receives at the fold line from circumferences is reduced, whereby the fold line is less likely to remain in the sheet-shaped absorbent layer. Moreover since the fiber assembly layer has the opening on the fold line, when the absorbent article is folded, the sheet-shaped absorbent layer comes to be folded at a part where the opening overlaps, and as a result, the pressure which the sheet-shaped absorbent layer receives at the fold line from circumferences is further reduced, whereby the fold line is less likely to remain in the sheet-shaped absorbent layer. Therefore, when the folded absorbent article is unfolded for use, a trace of the fold line is less likely to remain in the absorbent article, and as a result, the wearing feel of the absorbent article improves.

The opening means an opening which penetrate the fiber assembly layer in the thickness direction. The position of the opening of the fiber assembly layer is not particularly limited as long as the opening is provided on the fold line extending in the width direction. In the case that a plurality of fold lines are formed in the absorbent article, it is only necessary to provide the opening on at least one of the fold lines.

The fiber assembly layer may have only one opening or two or more openings. Preferably, the fiber assembly layer has one opening extending in the longitudinal direction of the absorbent body. In this case, the opening is preferably provided so as to cross a centerline in the longitudinal direction of the absorbent body. Thus, the fiber assembly layer preferably has the one opening extending in the longitudinal direction so as to cross both the fold line and the centerline of the absorbent body in the longitudinal direction. When the opening is provided in this manner, the opening tends to be positioned near an urethral orifice of a wearer in wearing, and thus, the wearer is less likely to feel a pressure around the urethral orifice due to the lowered rigidity of the absorbent article at the opening, thereby improving the wearing feel of the absorbent article. In addition, when the absorbent article is used, the trace of the fold line is less likely to remain at least near the urethral orifice in the sheet-shaped absorbent layer, thereby improving the wearing feel of the absorbent article. In the case that the fiber assembly layer has only one opening, the opening is preferably provided at the center of the absorbent body in the width direction.

In the case that the fiber assembly layer has only one opening, a width (a length in the width direction) of the opening is preferably 10% or more of a width of the fiber assembly layer at the fold line, more preferably 20% or more of the width of the fiber assembly layer at the fold line, and preferably 60% or less of the width of the fiber assembly layer at the fold line, more preferably 50% or less of the width of the fiber assembly layer at the fold line. When the width of the opening is 10% or more of the width of the fiber assembly layer at the fold line, the sheet-shaped absorbent layer is less likely to be pressed strongly in the absorbent article which is folded at the fold line on which the opening is provided. When the width of the opening is 60% or less of the width of the fiber assembly layer at the fold line, a body fluid such as urine tends to be rapidly absorbed by the fiber assembly layer, and the absorbent body is less likely to deform.

In the case that the fiber assembly layer has only one opening, a length of the opening in the longitudinal direction is preferably 20% or more of a length of the fiber assembly layer in the longitudinal direction, more preferably 30% or more of the length of the fiber assembly layer in the longitudinal direction, and preferably 70% or less of the length of the fiber assembly layer in the longitudinal direction, more preferably 60% or less of the length of the fiber assembly layer in the longitudinal direction. When the length of the opening in the longitudinal direction is 20% or more of the length of the fiber assembly layer in the longitudinal direction, the opening tends to be positioned near an urethral orifice of a wearer in wearing. When the length of the opening in the longitudinal direction is 70% or less of the length of the fiber assembly layer in the longitudinal direction, a bodily fluid tends to be rapidly absorbed by the fiber assembly layer, and the absorbent body is less likely deform.

As the pulp fibers contained in the fiber assembly layer, split pulp fibers are preferable. In addition, the split pulp fibers are preferably used in a form of a fiber mass. As the fiber assembly layer, a shaped product of an absorbent material such as pulp fibers, that is formed into a predefined shape, may be used, or an absorbent material wrapped with a covering sheet such as a paper (e.g., tissue paper) and a liquid-permeable nonwoven fabric may be used. Since the fiber assembly layer contains pulp fibers, the fiber assembly layer is excellent in softness, can rapidly absorb a body fluid such as urine, and provides excellent diffusion of the absorbed body fluid therein. Pulp fibers may reversibly hold body fluids, not absorbing and irreversibly fixing a body fluid like an absorbent polymer; however, in the present description, the term "absorb" includes the meaning of "hold".

The fiber assembly layer may contain an absorbent polymer in addition to the pulp fibers. The absorbent polymer is used as a kind of the absorbent material. As the absorbent polymer, an absorbent polymer which can be used in the sheet-shaped absorbent layer may be used. When the fiber assembly layer contains the absorbent polymer, the fiber assembly layer has an enhanced holding capacity of a bodily fluid.

When the fiber assembly layer contains the absorbent polymer, the content ratio of the absorbent polymer in the fiber assembly layer is preferably 40 mass % or less, more preferably 30 mass % or less, and even more preferably 20 mass % or less. When the content ratio of the absorbent polymer is 40 mass % or less, the fiber assembly layer is easily formed so as to be flexible. The lower limit of the content ratio of the absorbent polymer is not particularly specified. That is, the fiber assembly layer may not contain an absorbent polymer. Here, the content ratio of the absorbent polymer means the content ratio of the absorbent polymer in the absorbent material.

The fiber assembly layer may contain thermal-adhesive fibers such as polyolefin fibers (e.g., polyethylene and polypropylene), polyester fibers (e.g., PET), and polyamide fibers in addition to the pulp fibers. The thermal-adhesive fibers are used as a kind of the absorbent material. When the fiber assembly layer contains these fibers, the fiber assembly layer easily keeps its shape better. The thermal-adhesive fibers may be hydrophilized with a surfactant or the like in order to enhance the affinity for a bodily fluid such as urine.

The fiber assembly layer preferably has a mass per unit area of 90 g/m$^2$ or more, more preferably 100 g/m$^2$ or more, preferably 150 g/m$^2$ or less, and more preferably 140 g/m$^2$ or less. When the fiber assembly layer has a mass per unit of 90 g/m$^2$ or more, the fiber assembly layer sufficiently fulfill a function of absorbing a bodily fluid. When the fiber assembly layer has a mass per unit of 150 g/m$^2$ or less, the fiber assembly layer is not thickened excessively, and the fiber assembly layer which is easy to be folded is easily obtained.

In the absorbent laminate, which is formed by laminating the fiber assembly layer and the sheet-shaped absorbent layer, the order of laminating the fiber assembly layer and the sheet-shaped absorbent layer is not particularly limited. For example, the absorbent laminate may comprise the fiber assembly layer and the sheet-shaped absorbent layer in this order from the top sheet side. Alternatively, the absorbent laminate may comprise the fiber assembly layer and the sheet-shaped absorbent layer in this order from the back sheet side, that is, comprise the sheet-shaped absorbent layer and the fiber assembly layer in this order from the top sheet side. In each case, the fiber assembly layer is preferably provided adjacent to the sheet-shaped absorbent layer.

In the case that the absorbent laminate comprises the fiber assembly layer and the sheet-shaped absorbent layer in this order from the top sheet side, a bodily fluid such as urine which has passed through the top sheet and reached to the fiber assembly layer diffuses in the planar direction in the fiber assembly layer, and as a result, the bodily fluid comes to be easily absorbed by the sheet-shaped absorbent layer in a broad area. Therefore, the absorbent article can absorb a bodily fluid effectively.

In the case that the absorbent laminate comprises the sheet-shaped absorbent layer and the fiber assembly layer in this order from the top sheet side, a bodily fluid such as urine which has passed through the top sheet and reached to the absorbent laminate is absorbed first by the sheet-shaped absorbent layer. At this time, when the bodily fluid are excreted in a large amount at one time, the sheet-shaped absorbent layer may not fully absorb the bodily fluid, whereby a part of the bodily fluid tends to transfer to the fiber assembly layer. Since the fiber assembly layer has the excellent capability of rapidly absorbing a bodily fluid, the bodily fluid such as urine which has passed through the sheet-shaped absorbent layer is rapidly absorbed by the fiber assembly layer. In addition, in the case that the absorbent laminate comprises the sheet-shaped absorbent layer and the fiber assembly layer in this order from the top sheet side, the absorbent article is also excellent in preventing return (wet back) of a bodily fluid to a skin side. Since the sheet-shaped absorbent layer contains the absorbent polymer but does not contain a pulp fiber between the nonwoven fabric sheets, even when the sheet-shaped absorbent layer absorbs a bodily fluid, the surface thereof is kept relatively dry. On the other hand, when the fiber assembly layer absorbs a bodily fluid, the fiber assembly layer easily becomes wet, and there is the possibility that a part of the absorbed bodily fluid returns by the fiber assembly layer being pressed. However, when the sheet-shaped absorbent layer provided so as to be closer to the top sheet than the fiber assembly layer, the bodily fluid returning from the fiber assembly layer is easily prevented from reaching the skin of a wearer.

The absorbent laminate may comprise two or more fiber assembly layers. The absorbent laminate may also comprise two or more sheet-shaped absorbent layers. When the absorbent laminate comprises two or more fiber assembly layers and/or two or more sheet-shaped absorbent layers, the order of laminating the fiber assembly layers and the sheet-shaped absorbent layers are not particularly limited. The same kind of layers may be laminated so as to be next to each other, or different kinds of layers may alternately be laminated.

Preferably, the absorbent laminate comprises the sheet-shaped absorbent layer and the fiber assembly layer in this order from the top sheet side. That is, it is preferable that the sheet-shaped absorbent layer is provided on the top sheet side and the fiber assembly layer is provided on the back sheet side. When the sheet-shaped absorbent layer and the fiber assembly layer are laminated in this manner, the absorbent article which is excellent in a wearing feel and has a high absorptive capacity is easily obtained.

It is also preferable that the absorbent laminate comprises the sheet-shaped absorbent layer and the fiber assembly layer in this order from the top sheet side, and another sheet-shaped absorbent layer or another fiber assembly layer is provided on the back sheet side of the fiber assembly layer. That is, the absorbent laminate may comprise the first sheet-shaped absorbent layer, the fiber assembly layer and the second sheet-shaped absorbent layer in this order from the top sheet side; and the absorbent laminate may comprise the sheet-shaped absorbent layer, the first fiber assembly layer and the second fiber assembly layer in this order from the top sheet side. However, in light of ease of folding the absorbent article, it is preferable that the thickness of the absorbent article is thin, and thus, another layer provided on the back sheet side of the fiber assembly layer is preferably the sheet-shaped absorbent layer, if provided.

The shape (planar shape) of the absorbent laminate is not particularly limited. The shapes (planar shapes) of the fiber assembly layer and the sheet-shaped absorbent layer are not also particularly limited. The shapes of the fiber assembly layer and the sheet-shaped absorbent layer may be same or different from each other. The shapes of the fiber assembly layer and the sheet-shaped absorbent layer are determined as appropriate according to application, and examples of the shapes thereof include, for example, a rectangular shape, an hourglass shape, a center nipped-in gourd shape, and a battledore shape.

Embodiments of the absorbent article of the present invention are explained in the following, referring to drawings in which an incontinence pad is shown as an example. However, the present invention is not limited to the following embodiments.

Figure 1:
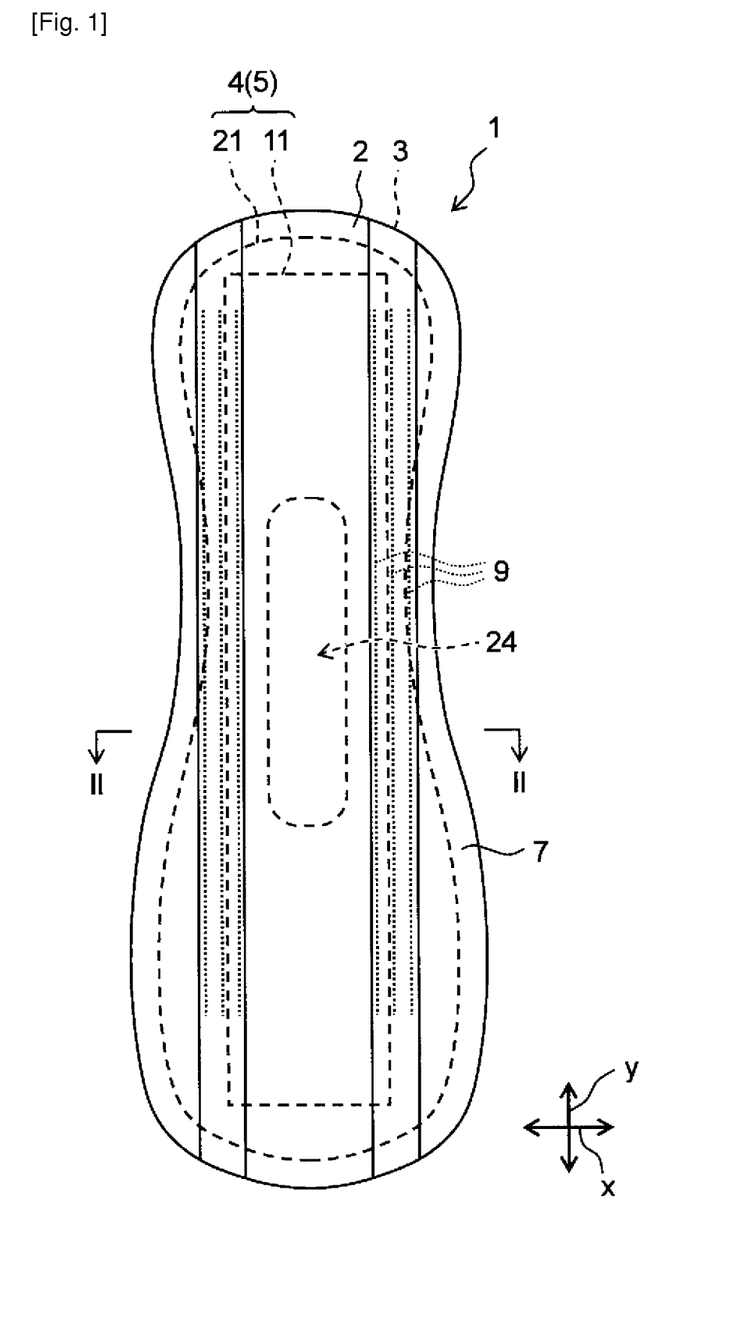
FIG. 1 shows a plan view of an incontinence pad (an absorbent article) in the unfolded state.
Figure 2:
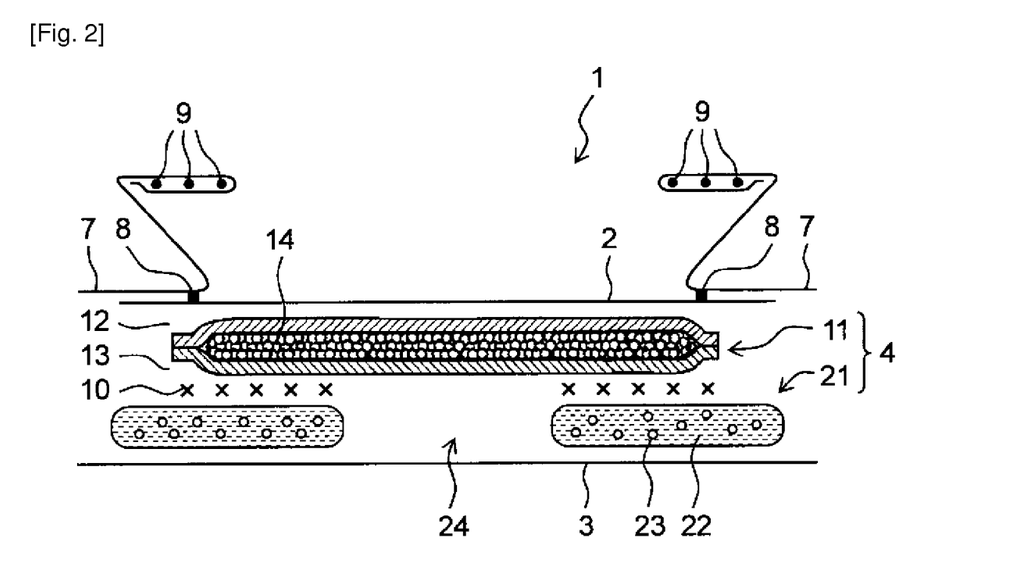
FIG. 2 shows a cross-sectional view taken along line II-II of the incontinence pad shown in FIG. 1

FIG. 1 shows a plan view of an incontinence pad in the unfolded state, as the absorbent article of the present invention. FIG. 2 shows a cross-sectional view taken along line II-II of the incontinence pad shown in FIG. 1. In the drawings, an arrow x represents the width direction and an arrow y represents the longitudinal direction. A direction on the plane formed by the arrows x and y is defined as the planar direction, and a direction orthogonal to the arrows x and y is defined as a thickness direction or a vertical direction.

The absorbent article 1 comprise an absorbent body 5 including a top sheet 2, a back sheet 3 and an absorbent laminate 4 disposed between the top sheet 2 and the back sheet 3. The absorbent body 5 has a longitudinal direction y and a width direction x. The top sheet 2 is placed so as to face to a wearer's skin, and allows a bodily fluid such as urine to permeate through. The bodily fluid which has passed through the top sheet 2 transfers to the absorbent laminate 4.

Side sheets 7, which extend in the longitudinal direction y, are provided to the top sheet 2 on both sides in the width direction x. The side sheet 7 is joined to the top sheet 2 at a joining portion 8. The side sheet 7 is preferably made of a liquid-impermeable plastic film, a liquid-impermeable nonwoven fabric, or the like. A rising elastic member 9 is disposed at an inner end in the width direction x of the each side sheet 7 (In FIGS. 1 and 2, three elastic member are disposed). When the disposable diaper 1 is worn, the inner end of the side sheet 7 rises toward a wearer's skin due to a shrinkage force of the rising elastic member 9, thereby preventing excrement such as urine from leaking.

The absorbent laminate 4 comprises a sheet-shaped absorbent layer 11 and a fiber assembly layer 21 in this order from the top sheet 2 side. The sheet-shaped absorbent layer 11 contains an absorbent polymer 14 but not containing a pulp fiber between nonwoven fabric sheets 12, 13. The fiber assembly layer 21 contains pulp fibers 22 and absorbent polymers 23. The fiber assembly layer 21 has an opening 24. The opening 24 is provided at the center of the absorbent body 5 in the width direction x and extends in the longitudinal direction y. The sheet-shaped absorbent layer 11 and the fiber assembly layer 21 are joined together by an adhesive layer 10.

Folding of the incontinence pad shown in FIGS. 1 and 2 is explained with reference to FIGS. 3A to 3C, 4, and 5A to 5D. In FIGS. 3A to 3C, 4, and 5A to 5D, the length of the opening 24 in the longitudinal direction y is shown to be varied according to the number of fold lines; however, the relation between the number of fold lines and the length of the opening 24 in the longitudinal direction y, and the positions of the fold lines are not limited to the embodiment shown in FIGS. 3A to 3C, 4, and 5A to 5D. In the embodiments shown in these drawings, the opening 24 is provided so as to cross the centerline of the absorbent body 5 in the longitudinal direction y.

Figure 3A:
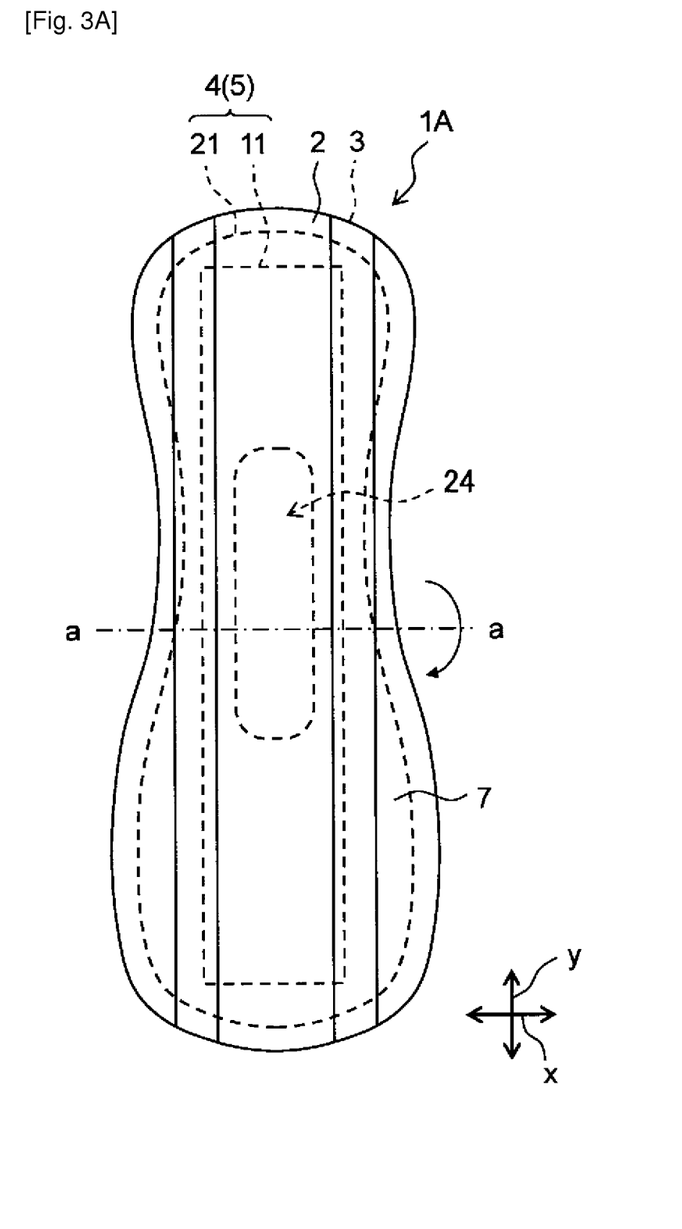
FIG. 3A shows an absorbent article which is to be folded in two.
Figure 3B:
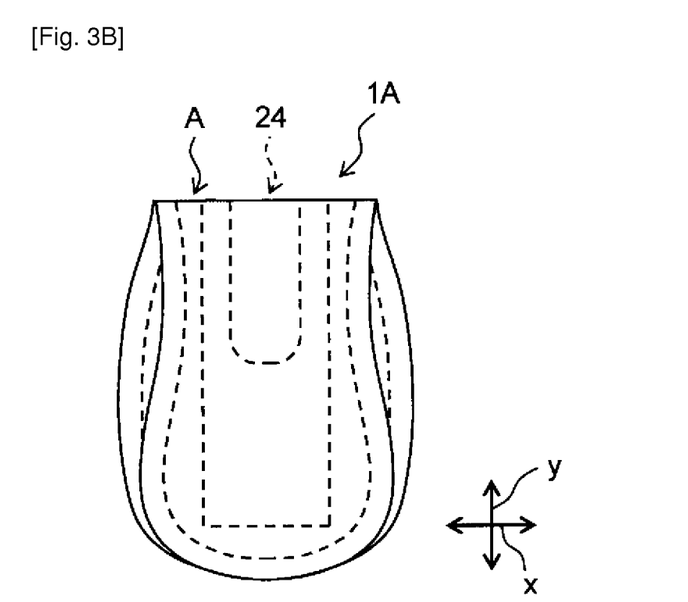
FIG. 3B shows an absorbent article folded in two.

FIG. 3A shows an absorbent article which is to be folded in two, and FIG. 3B shows an absorbent article folded in two. An absorbent article 1A shown in FIG. 3A is folded at a line a-a which extends in the width direction x to form a fold line A as shown in FIG. 3B. The absorbent article 1A is folded at one fold line A extending in the width direction x, thereby folded in two. In FIGS. 3A and 3B, the fold line A (the line a-a) coincides with the centerline of the absorbent body 5 in the longitudinal direction y. When the fold line A is formed at or near the centerline of the absorbent body 5 in the longitudinal direction y, the absorbent article 1A is folded compactly. In the absorbent article 1A, the opening 24 is provided on the fold line A, and thus, the sheet-shaped absorbent layer 11 is not strongly pressed at the fold line A when the absorbent article 1A is folded. Therefore, when the folded absorbent article 1A is unfolded for use, a trace of the fold line is less likely to remain in the sheet-shaped absorbent layer 11.

Figure 3C:
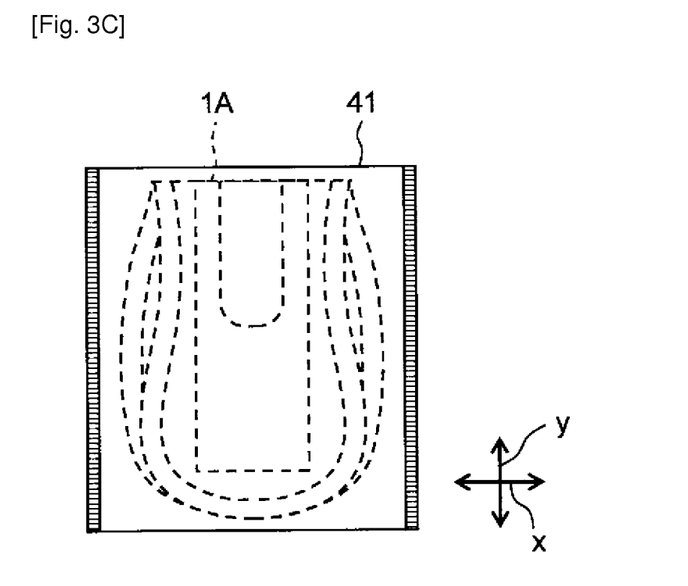
FIG. 3C shows an example of an individually wrapped absorbent article in which the absorbent article shown in FIG. 3B is wrapped with a wrapping material.

The folded absorbent article 1A may be wrapped with a wrapping material 41, as shown in FIG. 3C. The folded absorbent article 1A is wrapped with the wrapping material 41, whereby the absorbent article 1A comes to be individually wrapped. In such a case, the absorbent article 1A can be carried with ease, and can be easily put into a container.

Figure 4:
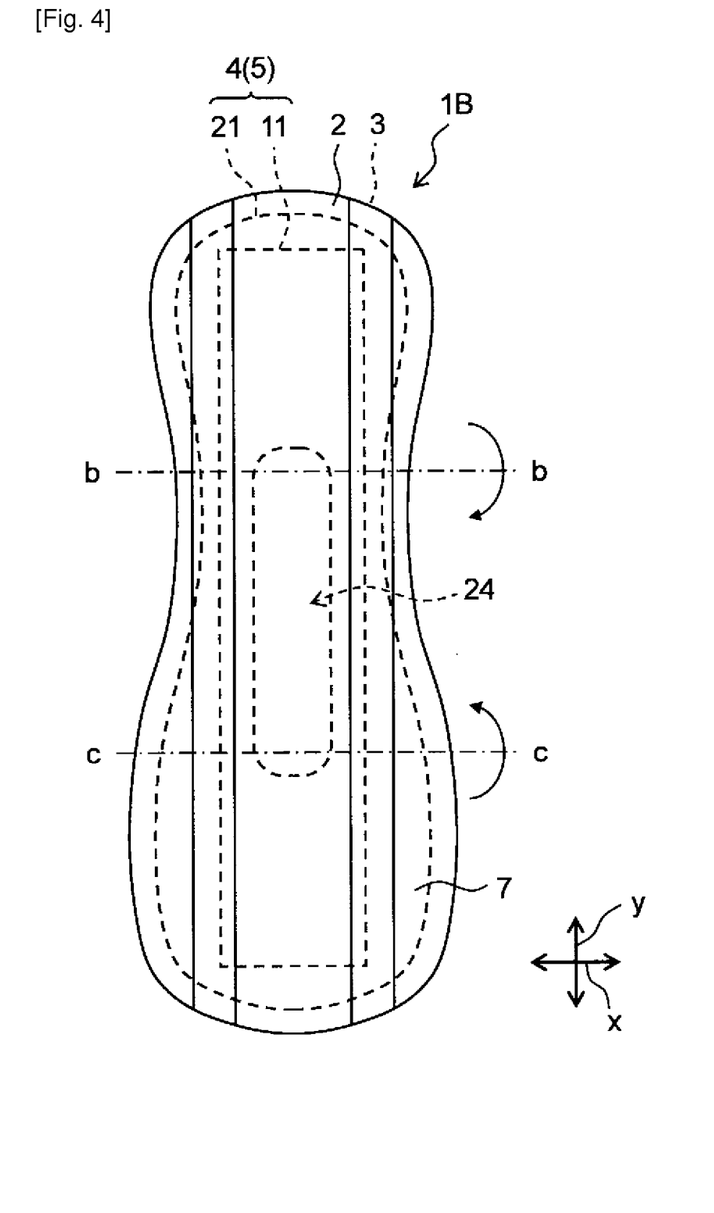
FIG. 4 shows an absorbent article which is to be folded in three.

FIG. 4 shows an absorbent article which is to be folded in three. The absorbent article 1B shown in FIG. 4 is folded at a line b-b and a line c-c which extend in the width direction x to form a fold line B (not shown) and a fold line C (not shown), respectively. In the absorbent article 1B, the opening 24 is provided so as to cross both the line b-b and the line c-c which extend in the width direction x. The absorbent article 1B shown in FIG. 4 is folded at two fold lines B and C extending in the width direction x, thereby obtaining the threefold absorbent article 1B. In the absorbent article 1B, since the opening 24 is provided astride the fold line B and the fold line C, the sheet-shaped absorbent layer 11 is not strongly pressed at the fold lines B and C when the absorbent article 1A is folded. Therefore, when the folded absorbent article 1B is unfolded for use, a trace of the fold line is less likely to remain in the sheet-shaped absorbent layer 11.

In FIG. 4, the opening 24 is provided across both the fold line B and the fold line C. However, in the case that a plurality of fold lines are formed in the absorbent article, it is only necessary to provide the opening on at least one of the fold lines. When FIG. 4 is taken as an example, the opening 24 only needs to be provided so as to cross at least one of the fold line B and the fold line C.

Figure 5A:
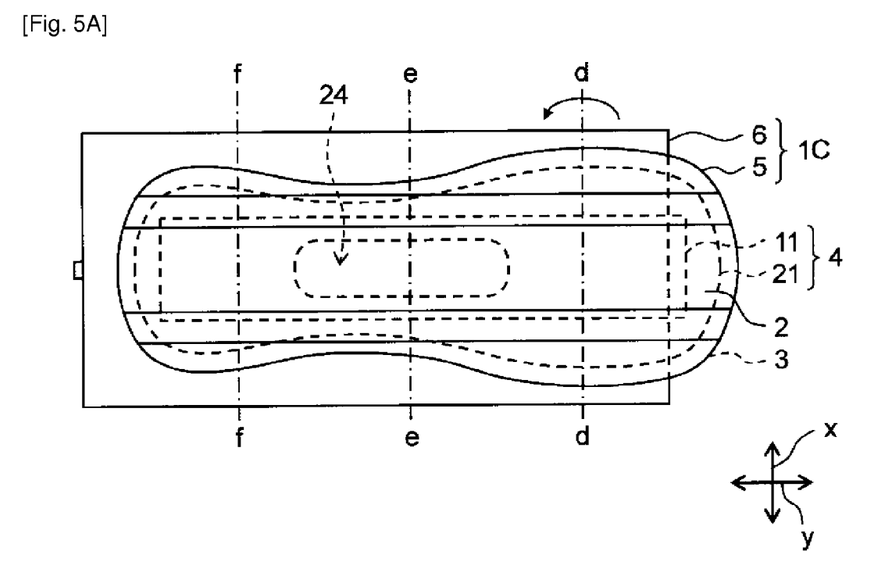
FIG. 5A shows an absorbent article which is to be folded in four.

FIG. 5A shows an absorbent article which is to be folded in four. The absorbent article 1C shown in FIG. 5A comprises an absorbent body 5 including a top sheet 2, a back sheet 3 and an absorbent laminate 4 between the top sheet 2 and the back sheet 3, and a cover sheet 6. The cover sheet 6 is detachably joined to the back sheet 3 by an adhesive layer. In FIG. 5A, the cover sheet 6 has a rectangular shape, extends beyond both edges of the absorbent body 5 in the width direction x, and extends beyond one edge of the absorbent body 5 in the longitudinal direction y. The cover sheet 6 only needs to extend beyond at least one edge of the absorbent body 5 in the longitudinal direction y, and may further extend beyond the other edge of the absorbent body 5 in the longitudinal direction y. When the cover sheet 6 is provided, as shown in FIG. 5A, the absorbent body 5 can be wrapped with the cover sheet 6 by folding the absorbent article 1C at fold lines extending in the width direction x. As a result, the absorbent article 1C which is folded and wrapped individually as shown in FIG.

Figure 5B:
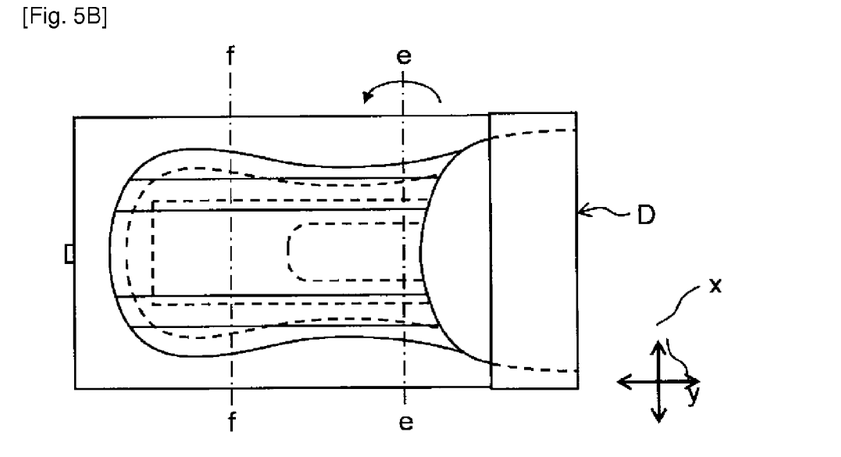
FIG. 5B shows an example of folding the absorbent article shown in FIG. 5A.
Figure 5C:
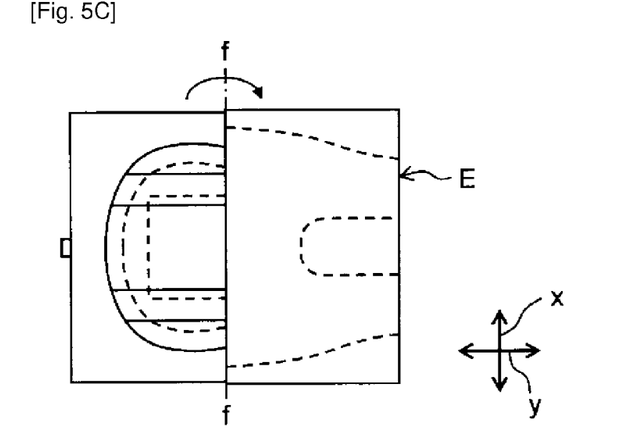
FIG. 5C shows an example of folding the absorbent article shown in FIG. 5B.
Figure 5D:
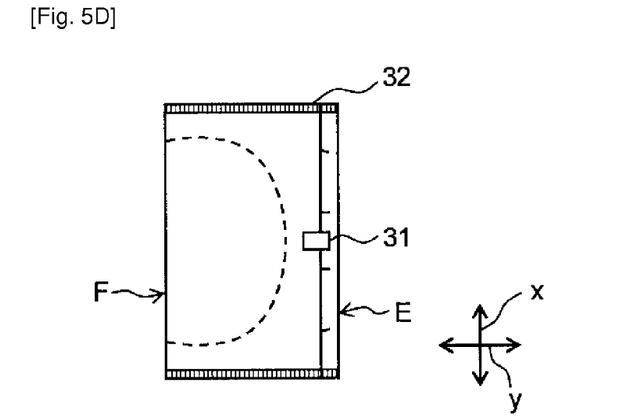
FIG. 5D shows an example of folding the absorbent article shown in FIG. 5C, and shows an absorbent article which is folded and individually wrapped with a cover sheet.

5D can be obtained. The individually wrapped absorbent article 1C can be carried with ease and can be easily put into a container. Further, the cover sheet 6 serves as a wrapping material for the absorbent article 1C, which is efficient.

The absorbent article 1C is folded at a line d-d, a line e-e, and a line f-f, which extend in the width direction x, to form a fold line D, a fold line E, and a fold line F, respectively. In the absorbent article 1C, the cover sheet 6 is folded at respective fold lines together with the absorbent body 5. First, the absorbent article 1C is folded at the line d-d to form the fold line D, then folded at the line e-e to form the fold line E, and then folded at the line f-f to form the fold line F. As a result, the absorbent article 1C is folded at the three fold lines D, E, and F extending in the width direction x, thereby folded in four, as shown in FIG. 5D.

In the absorbent article 1C in which the absorbent body 5 is wrapped with the cover sheet 6, the cover sheet 6 is preferably joined to itself at joining parts 32 located at both edges thereof in the width direction x. When the absorbent article 1C is wrapped in this manner, handleability of the individually wrapped absorbent article 1C is improved. Joining of the cover sheet 6 to itself may be performed by a known adhesive means such as, for example, an adhesive agent or heat sealing.

At one edge of the cover sheet 6 (one edge which is located outside the absorbent body 5 in the longitudinal direction y), a tab 31 is preferably provided. When the tab 31 is provided, the folded absorbent article 1C wrapped individually is easily unfolded by pulling the tab 31. It is preferred that the tab 31 is fixed at the one edge of the cover sheet 6 and an adhesive layer detachable from the cover sheet 6 is provided on the tab 31. When the adhesive layer is provided on the tab 31, handleability of the individually wrapped absorbent article 1C is improved, and the folded absorbent article 1C is easily unfolded by pulling the tab 31 for use of the absorbent article 1C.

In the absorbent article 1C, the opening 24 is provided on the fold line E, and thus, the sheet-shaped absorbent layer 11 is not strongly pressed at the fold line E when the absorbent article 1C is folded. Therefore, when the folded absorbent article 1C is unfolded for use, a trace of the fold line is less likely to remain in the sheet-shaped absorbent layer 11. Further, when the absorbent article 1C is wrapped individually as shown in FIG. 5D, the fold line E on which the opening 24 is provided can be easily pinched, thereby improving handleability of the absorbent article 1C.

In FIG. 5D, the absorbent article 1C in which the absorbent body 5 is wrapped with the cover sheet 6 is shown; however, the embodiment in which the absorbent body is wrapped with the cover sheet is not limited to the absorbent article which is folded in four as shown in FIG. 5D. Further, in FIG. 3C, the absorbent article 1A wrapped with the wrapping material 41 is shown; however, the embodiment in which the absorbent article is wrapped with the wrapping material is not limited to the absorbent article which is folded in two as shown in FIG. 3C.

In FIGS. 3A to 3C, 4 and 5A to 5D, the absorbent article which is folded at one, two, or three fold line(s) extending in the width direction is shown; however, the number of the fold lines at which the absorbent article is folded is not limited to these numbers. Despite this, it is preferred that the number of the fold line is not excessively large, because the sheet-shaped absorbent layer comes to be not folded at excessively number of the fold line, the folded absorbent article can be carried with ease, and packing efficiency of the folded absorbent article in a container is improved. Therefore, in these respects, the number of the fold line is preferably not more than three. Thus, in the absorbent article, it is preferable that the absorbent article is folded at the one, two or three fold line(s) extending in the width direction, thereby folded in two, three or four.

The preferable embodiment of the sheet-shaped absorbent layer in the absorbent article of the present invention is explained in the following. It is preferable that the sheet-shaped absorbent layer has a plurality of absorbent polymer present regions, in each of which the absorbent polymer is provided, and an absorbent polymer absent region adjacent to the absorbent polymer present region between the nonwoven fabric sheets; and the nonwoven fabric sheets are joined together at the absorbent polymer absent region to form a sealing portion. When the nonwoven fabric sheets are joined together at the sealing portion, a bodily fluid easily pass through the absorbent polymer absent region, and as a result, the bodily fluid is easily absorbed from both the upper and lower sides of the sheet-shaped absorbent layer, whereby rapid absorption of a bodily fluid by the sheet-shaped absorbent layer is achieved. Further, the sealing portion serves to spread a bodily fluid in the planar direction on the surface of the sheet-shaped absorbent layer. Therefore, a bodily fluid spread in the planar direction is easily absorbed by the absorbent polymer of the sheet-shape absorbent layer or easily passes through the sheet-shape absorbent layer. The sealing portion may be formed by joining the nonwoven fabric sheets together by an adhesive or heat-sealing (thermal fusion-bonding).

In order that the sheet-shaped absorbent layer facilitates to be folded and the trace of the fold line is less likely to remain in the sheet-shaped absorbent layer, the content of the absorbent polymer at the region where the absorbent polymer is provided in the sheet-shape absorbent layer (the absorbent polymer present region), is preferably 400 $g/m^2$ or less, and more preferably 385 $g/m^2$ or less. Meanwhile, in order to ensure sufficient absorption amount in the absorbent polymer present region of the sheet-shaped absorbent layer, the content of the absorbent polymer in the absorbent polymer present region is preferably 100 $g/m^2$ or more, and more preferably 150 $g/m^2$ or more.

The absorbent polymer present regions are preferably disposed intermittently in the width direction of the absorbent body. When the absorbent polymer present regions are disposed intermittently in the width direction of the absorbent body, the sheet-shaped absorbent layer is easily folded by folding the absorbent article. In addition, when the folded absorbent article is unfolded for use, the trace of the fold line is less likely to remain in the sheet-shaped absorbent layer. Further, when the absorbent polymer present regions are disposed intermittently in the width direction of the absorbent body, a bodily fluid easily spreads in the longitudinal direction in the sheet-shaped absorbent layer. In general, the absorbent body is longer in the longitudinal direction than in the width direction, and therefore, when a bodily fluid spreads in the longitudinal direction, the bodily fluid is easily absorbed by the sheet-shaped absorbent layer rapidly.

Preferably, each of the absorbent polymer present regions is disposed in a practically rectangular shape being longer in the longitudinal direction of the absorbent body and having a length of 75% or more of the sheet-shaped absorbent layer in the longitudinal direction, and the absorbent polymer present regions are aligned practically parallel each other in the width direction of the absorbent body. When the absorbent polymer present regions are disposed in this manner, a bodily fluid easily spreads in the longitudinal direction in the sheet-shaped absorbent layer. In addition, in manufacturing the sheet-shaped absorbent layer continuously, it becomes easy to form the absorbent polymer present region by applying an absorbent polymer on a nonwoven fabric. The length of the rectangular shaped absorbent polymer present region is preferably 80% or more of the length of the sheet-shaped absorbent layer in the longitudinal direction, and more preferably 90% or more of the length of the sheet-shaped absorbent layer in the longitudinal direction.

Preferably, an adhesive is applied to the nonwoven fabric sheets of the sheet-shaped absorbent layer to form adhesive layers, and the absorbent polymer disposed at the absorbent polymer present region is fixed to the nonwoven fabric sheet by the adhesive layer. It is sufficient that at least a part of the absorbent polymer provided is fixed to the adhesive layer, and for example, the absorbent polymer in contact with the adhesive layer may be fixed to the adhesive layer. When the absorbent polymer is fixed to the nonwoven fabric sheets by the adhesive layer, the absorbent polymer is less likely to be unevenly located in the sheet-shaped absorbent layer, whereby folding of the sheet-shaped absorbent layer becomes easy. Here, the adhesive layer is preferably formed into a net-like structure for enhancing flexibility of the sheet-shaped absorbent layer. As the adhesive used for the adhesive layer, a rubber adhesive such as a natural rubber, a butyl rubber and polyisoprene; or a styrene elastomer such as styrene-isoprene-styrene block copolymer (SIS), styrene-butadiene-styrene block copolymer (SBS), styrene-ethylene-butadiene-styrene block copolymer (SEBS), and styrene-ethylene-propylene-styrene block copolymer (SEPS) is preferably used, since they are excellent in flexibility and adhesiveness after being cured.

Figure 6:
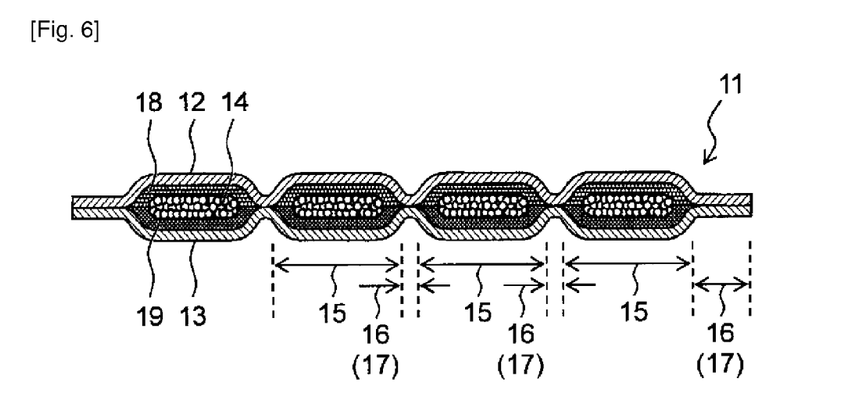
FIG. 6 shows a preferable example of a cross-sectional view of the sheet-shaped absorbent layer.

FIG. 6 shows an example of a cross-sectional view of the sheet-shaped absorbent layer, that is a preferred embodiment. A sheet-shaped absorbent layer 11 comprises a first nonwoven fabric sheet 12, a second nonwoven fabric sheet 13, a first adhesive layer 18 formed by applying an adhesive to the first nonwoven fabric sheet 12, a second adhesive layer 19 formed by applying an adhesive to the second nonwoven fabric sheet 13, and absorbent polymers 14 disposed between the first adhesive layer 18 and the second adhesive layer 19. The sheet-shaped absorbent layer 11 has a plurality of absorbent polymer present regions 15 and absorbent polymer absent regions 16 adjacent to the absorbent polymer present region 15. The absorbent polymer present regions 15 are disposed intermittently in the width direction. Absorbent polymers 14 of the absorbent polymer present regions 15 are fixed to the first nonwoven fabric sheet 12 and the second nonwoven fabric sheet 13 by the first adhesive layer 18 and the second adhesive layer 19, respectively. At the absorbent polymer absent regions 16, the first nonwoven fabric sheet 12 and the second nonwoven fabric sheet 13 are joined together by the first adhesive layer 18 and the second adhesive layer 19 to form sealing portions 17.

An absorbent article packaging of the present invention is explained in the following. The absorbent article packaging of the present invention comprises a container and a plurality of the absorbent articles of the present invention in the container.

The container is not particularly limited as long as the container can contain absorbent articles, and examples of the container include a plastic film bag, a paper bag, a plastic hard container, and a corrugated fiberboard box.

The container has an openable part. In the absorbent article packaging of the present invention, when the openable part of the container is opened, the absorbent article contained in the container can be taken out. Examples of the openable part include a perforation, a cover, a flap, and an adhesive tape which seals an opening of the container.

The absorbent articles contained in the container are stacked so that the fold lines, on each of which the opening is provided, of all the absorbent articles face in a same direction. That is, each of the absorbent articles contained in the container is folded at one or more fold lines; the opening of the fiber assembly layer is provided on at least one of the fold lines of each folded absorbent article; and the folded absorbent articles are stacked so that the fold lines, on each of which the opening is provided, of all the absorbent articles face in the same direction.

The stacked absorbent articles are contained in the container so that the fold lines on which the openings provided face to the openable part of the container. Thus, the container has the openable part formed on a side to which the fold lines provided with the openings of the stacked absorbent articles face. Since the absorbent articles are contained in the container in this manner, even when the absorbent articles are contained in the container in the state where the absorbent articles are compressed, the pressure from the adjacent absorbent articles is reduced at the fold line on which the opening is provided, and hence a gap is likely to occur between the adjacent absorbent articles. Therefore, when the openable part of the container is opened for taking out the absorbent article, the fold line on which the opening is provided can be easily pinched, and thus, it is easy to take out the absorbent article from the container.

Figure 7A:
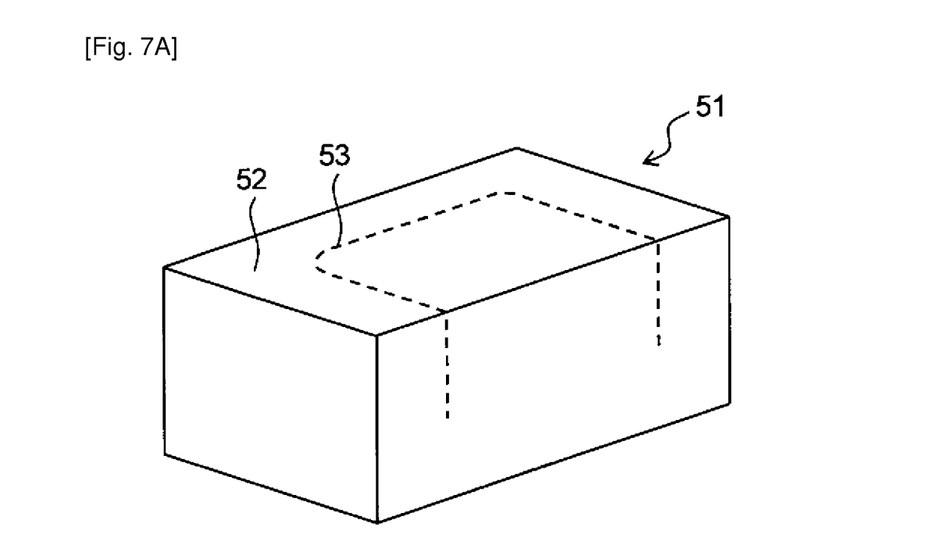
FIG. 7A shows an absorbent article packaging, in which a plurality of absorbent articles are contained in a container, in the state where an openable part is unopened.
Figure 7B:
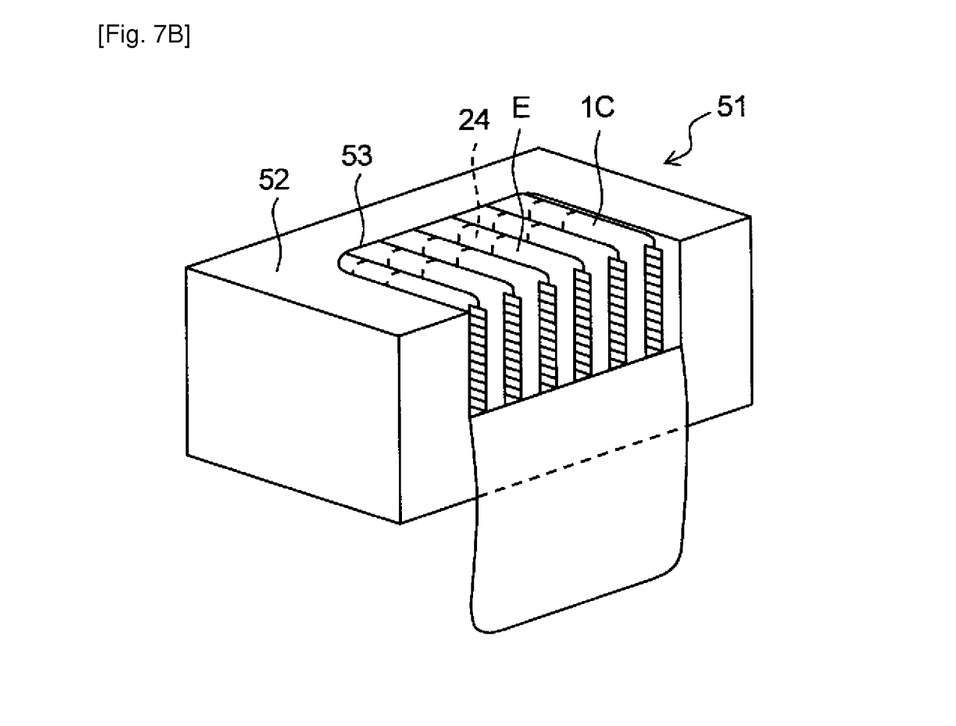
FIG. 7B shows an absorbent article packaging, in which a plurality of absorbent articles are contained in a container, in the state where an openable part is opened.

FIGS. 7A and 7B show an example of an absorbent article packaging in which absorbent articles are contained in a container. FIG. 7A shows an absorbent article packaging in the state where an openable part is unopened, and FIG. 7B shows the absorbent article package in the state where the openable part is opened. In FIGS. 7A and 7B, the absorbent articles 1C each wrapped with the cover sheet 6, as shown in FIG. 5D, are contained in the container 52.

The absorbent article packaging 51 comprising a container 52 and a plurality of the absorbent articles 1C contained in the container 52. The absorbent articles 1C are stacked in the container 52 so that the fold lines E, on each of which the opening 24 is provided, of all the absorbent articles 1C face in a same direction; and the container 52 has an openable part 53 formed on a side to which the fold lines E provided with the openings 24 of the stacked absorbent articles 1C face. In FIGS. 7A and 7B, a perforation is formed as an openable part 53. Further, in FIGS. 7A and 7B, the openable part 53 of the container 52 is formed astride the side to which the fold lines E face, on which the openings 24 are provided, and an adjacent side thereof. In this manner, the openable part of the container only needs to be formed at least on the side to which the fold lines, on which the openings are provided, of the stacked absorbent article face.

In FIGS. 7A and 7B, the absorbent articles, each of which is wrapped with the cover sheet, are contained in the container. However, the absorbent articles contained in the container are not limited thereto, and may be, for example, the absorbent articles which are merely folded, as shown in FIG. 5B, or the absorbent articles which are folded and wrapped with wrapping materials, as shown in FIG. 5C.

REFERENCE SIGNS LIST

1: an absorbent article (an incontinence pad)
2: a top sheet
3: a back sheet
4: an absorbent laminate
5: an absorbent body
6: a cover sheet
11: an sheet-shaped absorbent layer 21: a fiber assembly layer
12, 13: a nonwoven fabric sheet
14, 23: an absorbent polymer
22: pulp fibers
24: an opening
51: an absorbent article packaging
52: a container
53: an openable part

The invention claimed is:

1. An absorbent article comprising an absorbent body including a top sheet, a back sheet and an absorbent laminate disposed between the top sheet and the back sheet, wherein:
   the absorbent body has a longitudinal direction and a width direction;
   the absorbent laminate comprises a fiber assembly layer containing pulp fibers, and a sheet-shaped absorbent layer containing an absorbent polymer but not containing a pulp fiber between nonwoven fabric layers;
   the absorbent article is folded at a fold line extending in the width direction; and
   the fiber assembly layer has only one hole in the fiber assembly layer on the fold line, wherein the hole extends in the longitudinal direction of the absorbent body at a center of the absorbent body in the width direction.

2. The absorbent article according to claim 1, wherein:
   the absorbent article is folded at the one, two or three fold line(s) extending in the width direction, thereby folded in two, three or four; and
   the hole is provided on at least one of the fold line(s).

3. The absorbent article according to claim 1, further comprising a cover sheet detachably joined to the back sheet by an adhesive layer, wherein
   the cover sheet is folded at the fold line together with the absorbent body, and
   the absorbent body is wrapped with the cover sheet.

4. An absorbent article packaging comprising a container and the absorbent article according to claim 3, wherein:
   a plurality of the absorbent articles are stacked in the container so that the fold lines, on each of which the hole is provided, of all the absorbent articles face in a same direction; and
   the container has an openable part formed on a side to which the fold lines provided with the hole of the stacked absorbent articles face.

5. An absorbent article packaging comprising a container and the absorbent article according to claim 1, wherein:
   a plurality of the absorbent articles are stacked in the container so that the fold lines, on each of which the hole is provided, of all the absorbent articles face in a same direction; and
   the container has an openable part formed on a side to which the fold lines provided with the hole of the stacked absorbent articles face.

6. The absorbent article according to claim 1, wherein the absorbent article is folded only at a fold line extending in the width direction.

7. The absorbent article according to claim 1, wherein the absorbent laminate is folded at the one, two or three fold line(s) extending in the width direction, thereby folded in two, three or four; and the hole is provided on at least one of the fold line(s).

8. The absorbent article according to claim 1, wherein the hole is provided so as to cross both the fold line and a centerline of the absorbent body in the longitudinal direction.

9. The absorbent article according to claim 1, wherein a width of the hole is 10% or more and 60% or less of a width of the fiber assembly layer at the fold line.

10. The absorbent article according to claim 1, wherein a length of the hole in the longitudinal direction is 20% or more and 70% or less of a length of the fiber assembly layer in the longitudinal direction.

* * * * *